United States Patent
Lemaitre et al.

(10) Patent No.: US 6,905,516 B1
(45) Date of Patent: Jun. 14, 2005

(54) CALCIUM PHOSPHATE BONE SUBSTITUTE

(75) Inventors: Jacques Lemaitre, Lausanne (CH); Stéphane Terrazzoni, Morges (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 09/979,041

(22) PCT Filed: May 17, 2000

(86) PCT No.: PCT/CH00/00275

§ 371 (c)(1),
(2), (4) Date: Jan. 2, 2002

(87) PCT Pub. No.: WO00/71178

PCT Pub. Date: Nov. 30, 2000

(30) Foreign Application Priority Data

May 19, 1999 (CH) ................................................ 935/99

(51) Int. Cl.[7] .................................................. A61F 2/28
(52) U.S. Cl. .................................. 623/23.56; 623/23.62
(58) Field of Search ................................ 623/16, 23.62, 623/23.56

(56) References Cited

U.S. PATENT DOCUMENTS 5,525,148 A    6/1996  Chow et al.
5,531,794 A    7/1996  Takagi et al.

FOREIGN PATENT DOCUMENTS

| | | |
|---|---|---|
| EP | 0 551 611 A1 | 7/1993 |
| WO | WO 97/17285 | 5/1997 |

Primary Examiner—Cary E. O'Connor
Assistant Examiner—Candice C. Melson
(74) Attorney, Agent, or Firm—Nixon & Vanderhye, P.C.

(57) ABSTRACT

The invention concerns a bone substitute with controlled anatomical shape and macroporous structure made from chemically consolidated cement phosphocalcic materials. Said substitute can be obtained by forming a liquid or plastic paste consisting of calcium phosphate and other hardly soluble calcium slats. The forming by molding used with a paste and its chemical consolidation ex-vivo enables an entity to obtain a substitute having a more or less large size whereof the controllable anatomical shape corresponds to that of the bone block to be replaced, and an adapted macroporous architecture promoting rehabitation and resproption of the substitute, while ensuring the best initial mechanical properties and their being preserved until the graft is definitely replaced by the newly formed bone. The invention also concerns various methods of producing the mold and the pore-forming phase which respectively define the geometry and the porous architecture of the substitute during the forming by cast molding or injecting of a phosphocalcic paste.

16 Claims, 14 Drawing Sheets

CALCIUM PHOSPHATE BONE SUBSTITUTE

Figure 1:
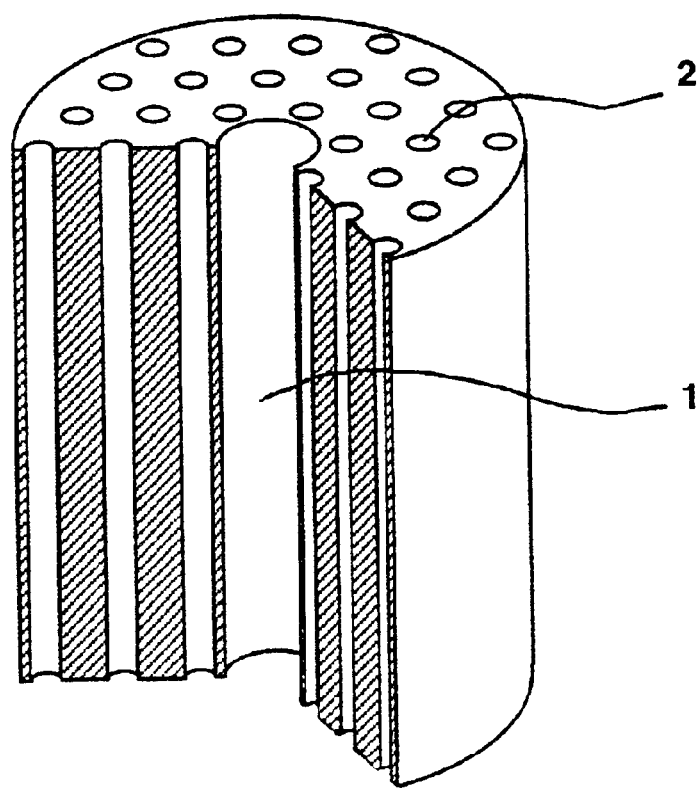

This application is the US national phase of international application PCT/CH00/00275 filed May 17, 2000 which designated the U.S. and claims benefit of CH 00935/99, dated May 19, 1999, the entire content of which is hereby incorporated by reference.

FIELD OF THE INVENTION

The present invention relates to a bone substitute made of chemically consolidated cementitious calcium phosphate materials, possessing an anatomic shape and a controlled macroporosity. The bone substitute can be obtained by shaping a liquid or plastic paste composed of calcium phosphates and other sparingly soluble salts. By molding the paste and its subsequent chemical hardening ex vivo, bone substitutes can be obtained with the following features: size and anatomic shape matching at will the bone defect to be replaced; adequately designed macroporous architecture promoting fast bone ingrowth into, and resorption of the bone substitute, while ensuring the best possible mechanical stability until complete replacement of the bone substitute by newly formed bone. The invention relates also to various processes for manufacturing molds and porogenic phases allowing to obtain the desired external geometries and macroporous architectures, upon shaping by casting or injection molding of calcium phosphate cementitious pastes.

This type of bone substitute can be used as synthetic bone graft (resorbable object) as well as permanent bone implants (non resorbable bone substitute), applicable within a large field of clinical indications thanks to their composition, their macroscopic (size, anatomic shape), and their microscopic characteristics (macroporous architecture, microporosirty) which can be tailored at will. The bone substitute according to the present invention can also be used as carrier for in vitro culture of bone cells.

State of the Art

In the context of the repair and replacement of hard tissue defects in the skeleton, orthopaedic surgeons and traumatologists are more and more incited to look for new synthetic materials capable to replace with advantage traditional bone grafts. Indeed, the field of application of traditional bone grafts is restricted to the filling of small size defects; besides ethical and legal issues, allografts (taken form a human donor) can cause immunologic problems and are subject to a risk of viral disease transmission; bone xenografts (taken from animals) are not only subject to the same problems as allografts, but also present a significant risk of transmitting prion diseases such as the bovine spongiform encephalopathy. Thus, several studies have been focused on synthetic bone substitution materials based on calcium phosphates. The chemical composition of such materials is close to that of the mineral fraction of bone tissues, ensuring so their perfect biocompatibility. Moreover, in contrast to inert ceramic materials such as alumina or zirconia, calcium phosphate are bioactive and osteoconductive, i.e. they interact positively with the cells of the host bone and promote osteogenesis. Calcium phosphate bone substitutes are mainly found on the market in the form of ceramics and cements. are subject to a risk of viral disease transmission; bone xenografts (taken from animals) are not only subject to the same problems as allografts, but also present a significant risk of transmitting prion diseases such as the bovine spongiform encephalopathy. Thus, several studies have been focused on synthetic bone substitution materials based on calcium phosphates. The chemical composition of such materials is close to that of the mineral fraction of bone tissues, ensuring so their perfect biocompatibility. Moreover, in contrast to inert ceramic materials such as alumina or zirconia, calcium phosphate are bioactive and osteoconductive, i.e. they interact positively with the cells of the host bone and promote osteogenesis. Calcium phosphate bone substitutes are mainly found on the market in the form of ceramics and cements.

There are three main bioceramic compositions (de Groot et al. 1983): hydroxyapatite ceramics ($Ca_5(PO_4)_3OH$, HAp) exhibit little resorbability in biological conditions (Jarcho et al. 1981); $\beta$-tricalcium phosphate ceramics ($Ca_3(PO_4)_2$, $\beta$-TCP) are more soluble than HAp in physiological conditions and their resorption in biological fluids has been demonstrated (Eggli et al. 1988); biphasic calcium phosphate ceramics, made of mixtures of HAp and $\beta$-TCP, exhibit intermediate resorbability depending on the exact composition of the mixture (LeGeros et coil. 1988). The biological behaviour of calcium phosphate ceramics depends on their physico-chemical characteristics, and specifically on their Ca/P atomic ratio. It has also been shown that intimate contact with host bone an fast recolonization by new bone of ceramic implants were promoted by the presence of macropores in the implant material. Moreover, the size of the macropores, and the size and number of interconnexions between the macropores have been shown to affect significantly the bone recolonization process (Fabbri et al. 1994). Thus, several processe have been developed for synthesizing bioceramic parts incorporating a more or less controlled macroporous architecture. Macroporous ceramics are generally obtained by adding porogenic agents, such as naphtalene or camphor particles, polymer microbeads (of polyethylene, polymethyl metacrylate, PVB . . . ) and the like, during the shaping step of the ceramic part by slip casting or dry pressing (Jarco et al. 1981; Driskell et al. 1973). The porogenic particles are sublimated or thermally decomposed before the final thermal densification treatment, thus leaving their mark in the form of pores in the final ceramic product. Another way of generating pores based on the use of corals has also been reported (White and Schors, 1986). Other techniques, such as those reported in the European patent application EP-A-253506 or in the international patent application WO 98/38949 are also applicable. Another possible way for obtaining calcium phosphate bodies with interconnected macroporosity is to exchange the carbonate ions of a coral block against orthophosphate ions in aqueous solutions of phosphates under high temperature and pressure; the so obtained ceramic parts have the cristallographic structure of HAp and the porous structure of the parent coral. It must be stressed, however, that calcium phosphate macroporous ceramics, despite their open porous architecture, exhibit little biological activity due to the high temperature treatments used for their consolidation. It is thus necessary to introduce in such ceramics a high pore volume fraction in order to accelerate significantly the bone recolonisation and resorption processes. Another drawback of the state-of-the-art ceramic shaping processes is their inability to achieve full control of the ceramic macroporous architecture. In fact, using conventional techniques makes it is very difficult to define independently the macroporous volume fraction and geometry. Shaping processes using naphtalene microbeads as porogenic agent can serve to illustrate this point: since interpore connexions only appear at the contacts between microbeads, it is necessary in this case to introduce a very high macroporosity (usually higher than 60% volume) to develop the number and size of interconnexions large enough to allow adequate bone ingrowth. Such a high porosity weakens significantly the mechanical strength of the resulting ceramic implants: therefore, the use of such materials in clinical applications where bone grafts would undergo significant mechanical stress cannot be recommended.

Calcium phosphate materials also exist in the form of cements. The most widely used formulations at present are: mixtures of tetracalcium phosphate monoxide ($Ca_4O(PO_4)_2$, TTCP) and dicalcium phosphate ($CaHPO_4$, DCPA or $CaHPO_4.2H_2O$, DCPD), e.g. the BoneSource® HAp cement; mixtures of α-tricalcium phosphate (α-TCP), monocalcium phosphate monohydrate ($Ca(HPO_4)_2.H_2O$, MCPM) and calcium carbonate (Norian SRS® cement); cements based on α-TCP, DCPA and calcium carbonate mixtures, and finally cements based on mixtures of β-TCP and MCPM (Mirtchi A. A., Lemaitre J., & Terao N., Biomaterials, 1989). All these mixtures can spontaneously set and harden in physiological conditions after mixing with water or some adequate aqueous mixing solution. Thanks to their resorbability and osteoconductivity these so-called calcium phosphate hydraulic cements (CPHC) are very promising candidates for making synthetic bone grafts. These CPHCs are usually used in the form of injectable or moldable paste for temporary bone filling. They can be implanted by mini-invasive surgical techniques. They can also be used in the form of pre-shaped blocks hardened ex-vivo. In any case, their low-temperature chemical consolidation process (well below 900° C.) allows to obtain bone substitutes with superior bioactivity compared to implants with comparable compositions consolidated by high temperature sintering. Indeed, low-temperature processing help to keep a significant microporosity in CPHCs, which confer them a higher biological activity than sintered bioceramics, even though their lower compacity results in weaker mechanical strength.

U.S. Pat. No. A-5,714,103 describes bone implants based on CHPCs, made of a succession of stacked layers, which macroporous architecture mimicks the natural porosity of spongious bone.

State-of-the-art bone implants based on CPHCs still present several drawbacks. In particular, their macroporous architecture is not controlled with adequate accuracy.

DESCRIPTION OF THE INVENTION

The present invention aims at solving the problems mentioned above. It refers to a bone implant exhibiting anatomic shape and controlled macroporous architecture based on cementitous calcium phosphate materials, as well as to different processes allowing their production.

More specifically, the bone substitute according to the present invention is characterised by the fact that it includes at least two sets of interconnected channel systems, through which an accurately controlled macropourous architecture is achieved. The bone substitute according to the present invention can be shaped either by casting a liquid cement paste or by injecting a thick cement paste into some appropriate mold. The cement paste is composed of a mixture of calcium phosphates to which other sparingly soluble calcium salts can be added, together with other inorganic and organic additives acting as setting regulators, deflocculants or plasticizers. Special care must be taken during the preparation of the paste in order to achieve adequate flowability and wettability, needed for obtaining defect-free products. The mold allowing to define the anatomic shape of the bone substitute can be made from a template, using silicone rubber or plaster; alternatively, it can be made using available rapid prototyping processes such as stereolithography and 3D fused-jet printing. Moreover, various techniques allow to generate upon shaping a well controlled macroporous architecture which can be calculated so as to promote bone ingrowth into the bone substitute and its subsequent resorption, while preserving the highest possible initial mechanical properties and ensuring their stability over time upon complete implant resorption. The porogenic phase allowing to generate a controlled macroporous architecture upon shaping can be introduced, in the simplest cases, in the form of polymer threads or, for more elaborated porous architectures, using fast prototyping techniques. An adequate selection of the cement paste formulation helps to keep at a negligible level the dimensional changes that can occur during the chemical consolidation of the bone substitute, allowing so to make directly near-net shape implants. Moreover, such bone substitutes chemically consolidated at low temperature keep their full biological activity. They can be used as synthetic bone grafts in a large variety of applications, as their chemical composition, together with their macroscopic (size and anatomic shape) and microscopic characteristics (macroporous architecture and microporosity) are easily adaptable to specific needs.

CPHCs bone substitutes can be made from a liquid or plastic paste composed of calcium phosphates and sparingly soluble calcium salts to which various inorganic and organic additives can be added (setting regulators, deflocculants and plasticizers). The cement paste is formed by mixing the desired amount of an aqueous solution with at least two powdery solid coreactants, one more acidic and the other more basic; the starting coreactants dissolve in the mixing solution, while a new phase thermodynamically more stable precipitates out of the same solution in the form of entangled crystals providing mechanical consolidation. In the frame of the present invention, various well known cement formulations can be used. For instance, brushitic cements prepared from mixtures of β-TCP and MCPM consolidate rapidly at ambient temperature and are highly resorbable (Mirtchi A. A., Lemaître J. & Terao N. "Calcium phosphate cements for medical use: Study of the β-tricalcium phosphate-monocalcium phosphate system." Biomaterials, 10, 475–479, 1989; Ohura K., Bohner M., Hardouin P., Lemaître J., Pasquier G., Flautre B., & Blary M. C. "Resorption and bone formation of new β-tricalcium phosphate-monocalcium phosphate cements: an animal study." J. Biomed. Mater. Res. 30, 193–200, 1996). Besides, a new HAp cement, consolidated by heating mixtures of monetite (DCPA) and calcium carbonate (calcite, aragonite or vaterite) in a water-saturated atmosphere, has been specifically developed for the manufacture of bone substitutes according to the present invention. This new HAp cement is particularly well adapted for making bone substitutes by slip casting of liquid pastes into moulds and porogenic phases obtained by fast prototyping techniques (see example 2.2). Other already known cement formulations (e.g. Norian SRS®, BoneSource® HAp cement, α-BSM™ from Etex Corporation, CEMENTEK® from Teknimed, . . . ) can also be used in the frame of the present invention.

The bone substitute which is the object of the present invention possess an controlled anatomic shape with accurately defined dimensions. The size of the bone substitute can be varied at will from a few millimeters up to several tens of centimeters. It is designed so as to reproduce the anatomy of the bone defects to be replaced; more specifically, they can be made with the same outer dimensions, making easier their insertion within the receiving site. For instance, in the case of long bone defects such as bone diaphyses, a central channel mimicking the medullar channel can be made in the axis of bone substitute, with the aim of accelerating its vascularization after implantation.

The porous architecture of the bone substitute being the object of the present invention can be made of a main network of open elongated pores (also referred to as "channels"). To which can be added, according to cases, one or two further secondary arrays of pores interconnected to the main pore network. The main pore network can be deterministic (e.g. square arrangement) or random, preferably hexagonal. It can be oriented at will, for instance parallel to the main directions of mechanical stress that will be applied to the substitute: by this way, macroporous bone substitutes with the highest possible mechanical stability can be obtained. The pores of the main network consist in elongated, non-intersecting channels. For instance, these channels may be approximately cylindrical. The intersection of the said channels with a virtual plane normal to their direction consists in areas of equal sections which centers of inertia are mutually distant preferably by 0.6 to 2 mm. The perimeters of the channel sections consist in closed convex, approximately circular lines. The individual areas of the channel sections are comprised between $8 \; 10^{-3}$ and 0.8 $mm^2$, preferably between 0.1 et 0.3 $mm^2$. One or optionally two secondary pore networks connect the pores of the main network, with the aim to facilitate metabolic exchanges between the bulk of the bone substitutes and the physiological environment. Said pores consist in holes which may have a cylindrical shape, with a constant sectional area comprised between $3 \; 10^{-3}$ and $8 \; 10^{-3}$ $mm^2$. The mutual distances between the centers of inertia of orthogonal sections in the secondary pore networks are preferably comprised between 1.1 and 2.1 mm. The complete network of interconnected macropores may represent, according to cases, a volume fraction comprised between 10 and 70%, preferably between 30 and 60% of the total apparent volume of the bone substitute. The total porosity of the bone substitute prepared according to the present invention also includes the intrinsic microporosity of their constitutive CPHC, which, depending on the exact formulation used, may amount between 20 to 60% of the solid volume (excluding macroporosity); in total, the bone substitute may develop a total porosity comprised between 28 and 88% vol.

The bone substitute according to the present invention is made ex-vivo preoperatively. In a preferred embodiment of the present invention, firstly the cement paste (liquid or plastic) containing the powdery co-reactants are prepared with very high care in order to achieve adequate flowability and wettability which are essential for accurate molding. According to cases, the paste rheology and homogeneity can be optimised by adding hydrosoluble polymers, preferably biocompatible polymers such as polyacrylates or polysaccharides. The co-reacting powders are also submitted to various grinding and deagglomeration treatments, in order to improve their dispersability and achieve superior paste homogeneity.

Shaping of the bone substitute is effected by die-casting or injection molding. According to the desired anatomic shape, various procedures allow to make the mold into which the cement paste will be injected or cast. For simple geometries, the molds can be made directly of silicone rubber or of plaster of Paris using a machined metallic or wood model. More complex geometries can be made using fast prototyping: for example the fused-jet fast prototyping process developed by Sanders Prototype Inc, USA (e.g. Model-Maker II and ToolMaker II machines) is particularly well adapted. In this particular case, the shape of the mold is designed on the basis of 3-dimensional images prepared with some Computer Assisted Design software, or directly form digitalised images. Digital data are transferred to the computer controlling the fast prototyping machine in the form of standard data exchange formats, such as .IGES, .STL, .DXF, .HPP, .OBJ and the like. The Computer Assisted Machining software uses this information to pilot the fused-jet printer which constructs the desired mold by successive layers. The phase used for generating the macroporous architecture can consist in the simplest cases in polymer threads; fast prototyping should be used for more complex macroporous architectures. In the latter case, the porogenic phase is integrated in the mold and both are constructed simultaneously.

After molding, the ex-vivo consolidation of the bone implants is obtained by chemical reactions which can occur temperatures ranging from ambient temperature up to 121° C. Unmolding can be performed before or after the chemical consolidation step, depending on the exact cement formulation an on the nature of the mold and porogenic materials. Finally, the porogenic phase can be extracted either by simple mechanical extraction (e.g. polymer threads) or, in more complex situations, by thermal decomposition at temperatures below 900° C., by chemical attack or by dissolution in some adequate solvent.

The bone substitute made according to the present invention present many advantages. Firstly, thanks to the perfectly controlled characteristics (composition, shape, macroporous architecture) and to the resulting optimized mechanical stability , such a bone substitute can be used as synthetic bone grafts in various clinical applications. The present invention makes possible to prepare bone substitutes which geometry and macroporosity are optimized in such a way that said substitutes develop mechanical properties matching those of the bone tissue to be replaced, and particularly its elastic modulus; at the same time, the macroporous architecture of the bone substitutes promotes their fast resorption and rapid colonization by new bone. Thus, the use of macroporous CHPC bone substitutes can be contemplated as synthetic macrografts for clinical applications involving bone substitution in load-bearing sites (e.g. long bone lengthening, long bone replacement, spinal fusion).

The bone substitute can also be used after in-vitro immersion in bone-cell culture media. This step allows to start the colonisation of the bone substitute by autologous bone cells and new bone tissue before its implantation in the patient. The cell culture medium my contain various active molecules such as antibiotics and bone growth factors (e.g. Bone Morphogenic Proteins, Transforming Growth Factors and the like), with the aim of accelerate vascularization and bone cell proliferation in the bulk of the synthetic bone substitutes. It is also possible to use the bone substitute according to the present invention as scaffolds for in-vitro bone cell and bone tissue culture.

In contrast to injectable bone cements, the bone substitute according to the present invention is consolidated ex-vivo preoperatively. In such conditions, the geometrical characteristics of the bone substitute can be controlled at will: anatomic morphologies can be obtained by using an adequately shaped, easily made mold; optimal macroporosity can be introduced in the form of a porogenic phase with a well defined and optimized architecture. In contrast with thermally consolidated ceramics, the bone substitute according to the present invention is chemically consolidated at low temperatures, with no perceptible dimensional changes. Thus, the final shape, size and porous architecture of CPHC bone substitutes are accurately defined during the molding step and are not altered by the subsequent consolidation step. Moreover, the low temperature consolidation process confers to the bone substitute prepared according to the present invention a superior bioactivity, in contrast to bioceramics of similar compositions consolidated by high temperature sintering. Consequently, the bone substitute according to the present invention keeps a significant microporosity which promotes its bioresorption, allows its impregnation with various active molecules (e.g. antibiotics, bone morphogenic proteins, growth factors and the like). Hence, introducing a large amount of macropores is not necessary for improving significantly bone colonization of the substitute by new bone, which allows to minimize the mechanical weakening of the bone substitute.

The shaping technologies developed for the bone substitute according to the present invention allow to generate perfectly controlled macroporous architectures, which are the best compromise from the biomechanical and biological viewpoints. For instance, the main porous network can be oriented parallel to the main mechanical stress directions which the bone substitute shall have to face after implantation, improving so its initial mechanical stability. On the other hand, the bone substitute can be made with a fully interconnected macroporosity, which will keep fast colonization by new bone with lower macroporous volume fractions. Hence, higher mechanical performance can be achieved, in contrast to the state-of-the-art bioceramic substitutes, for which a satisfactory level of macropore interconnexion needs to introduce a very high macroporous volume fraction, typically above 70%. Moreover, the macroporous architecture of the bone substitute according to the present invention can be designed so as to promote its in depth colonization by new bone before implant degradation becomes significant. Hence, the bone substitute is mechanically reinforced by new bone ingrowth of new bone, thus keeping a good biomechanical functionality within the few postoperative weeks. Summarizing, thanks to geometrical optimization, the bone substitute made according to the present invention can be made with reduced macroporosity, enabling fast bone ingrowth without significant loss of mechanical stability.

The variety of processing techniques used for the production of the molds and of the bone implant according to the present invention (e.g. molds made of silicone rubber or plaster, porogenic phases made of polymer threads, molds and porogenic phases prepared at once by fast prototyping techniques and the like) allow to obtain any desirable geometries and macroporous architectures. More specifically, the fast prototyping process based on tridimensional fused-jet printing has several advantages: Firstly, computer-assistance improves the speed and flexibility of bone implant design (including mold and porogenic phase): for instance, the anatomic shape can be defined from digitalized medical images obtained by computerized tomodensitometry or NMR imaging; the interconnected macroporous architecture can be modelized in order to find the best possible compromise between mechanical stability and bone ingrowth rate. Moreover, this process allows to make complex bone substitutes with high dimensional accuracy.

The following Figures illustrate the present invention:

FIG. 1: Bone substitute according to a first variation of the present invention.

Figure 2:
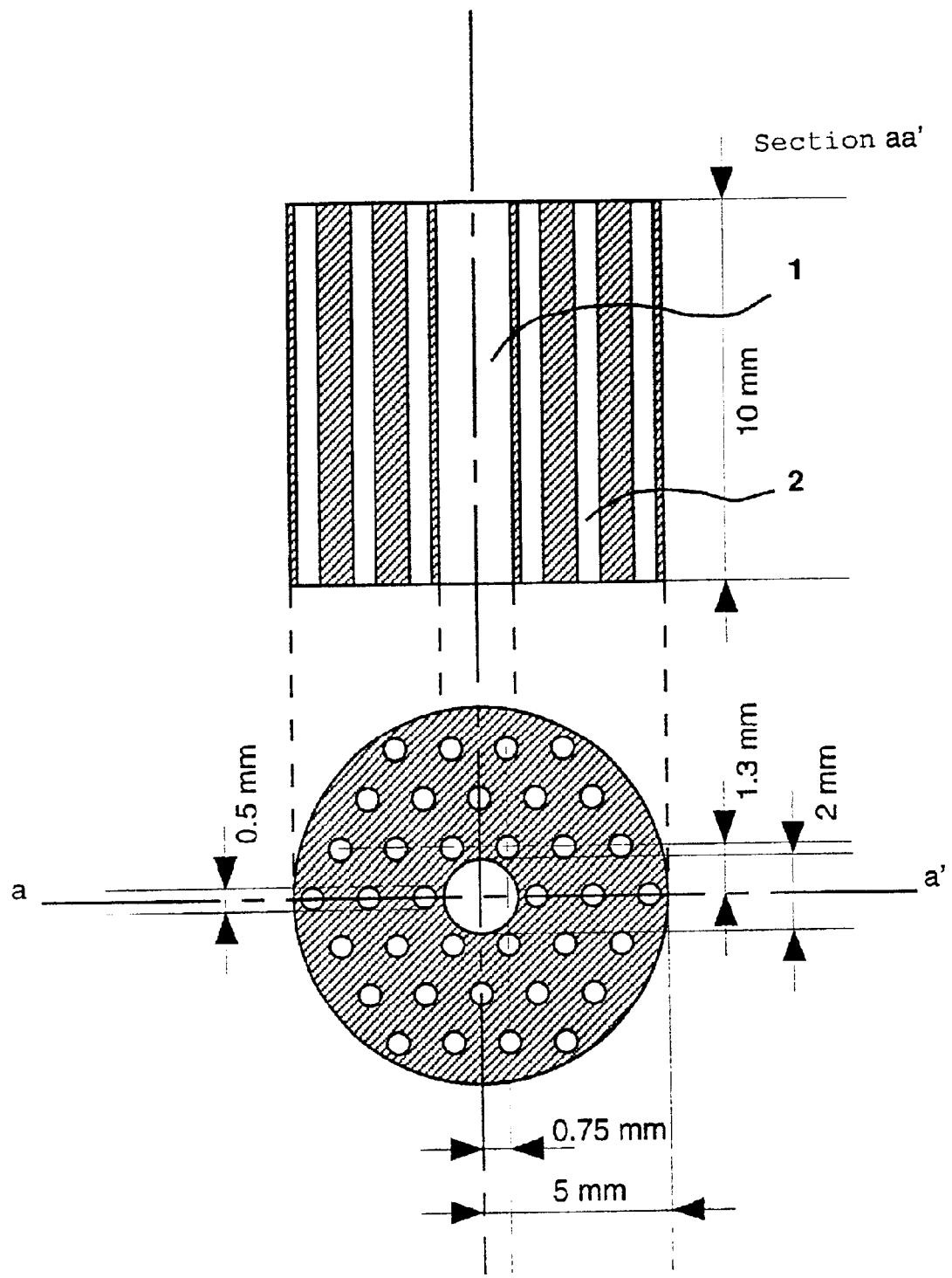

FIG. 2: Upper and front views of the bone substitute illustrated in FIG. 1

Figure 3:
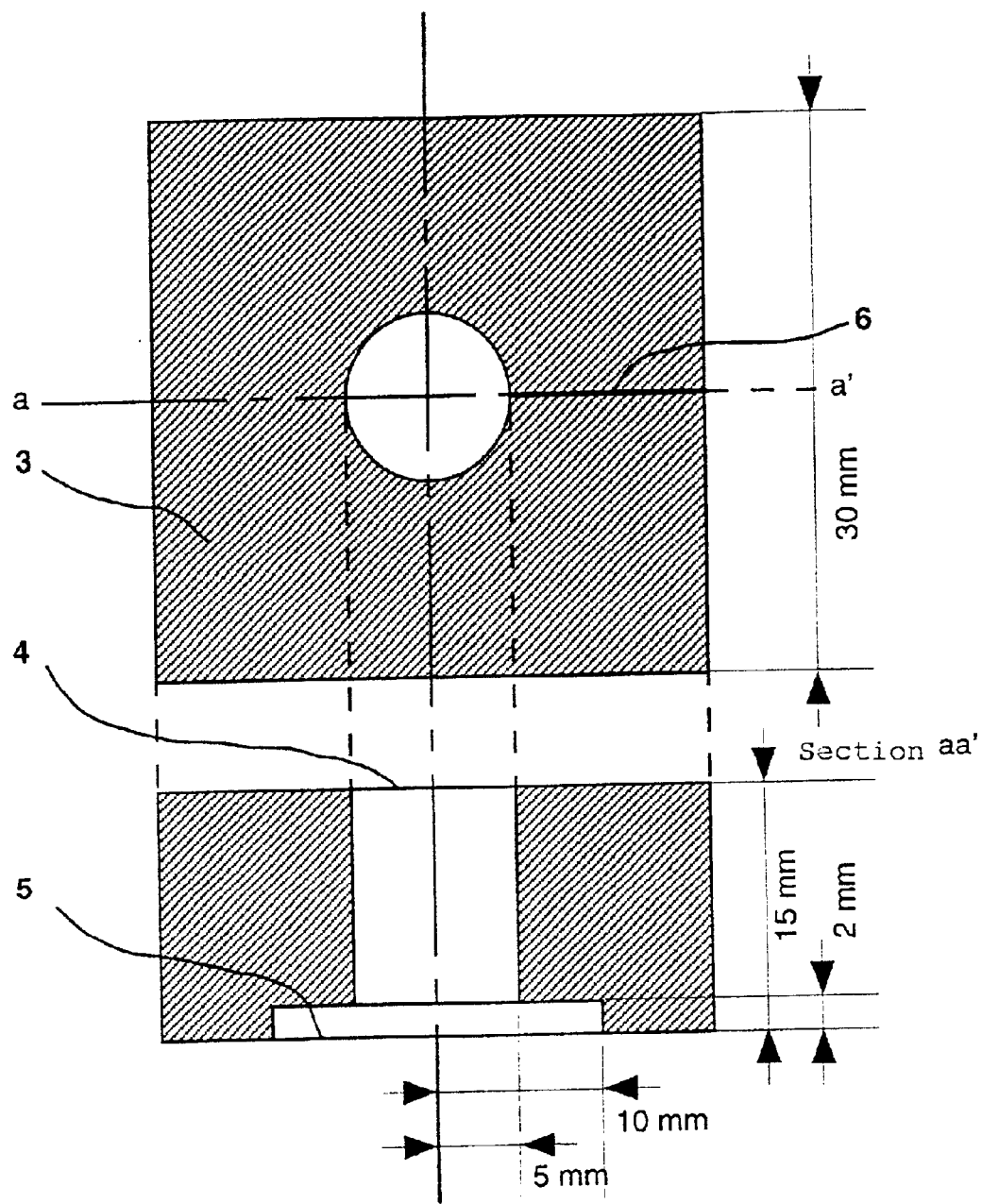

FIG. 3: Sketch of the mold used for producing the bone substitute illustrated in FIGS. 1 and 2.

Figure 4:
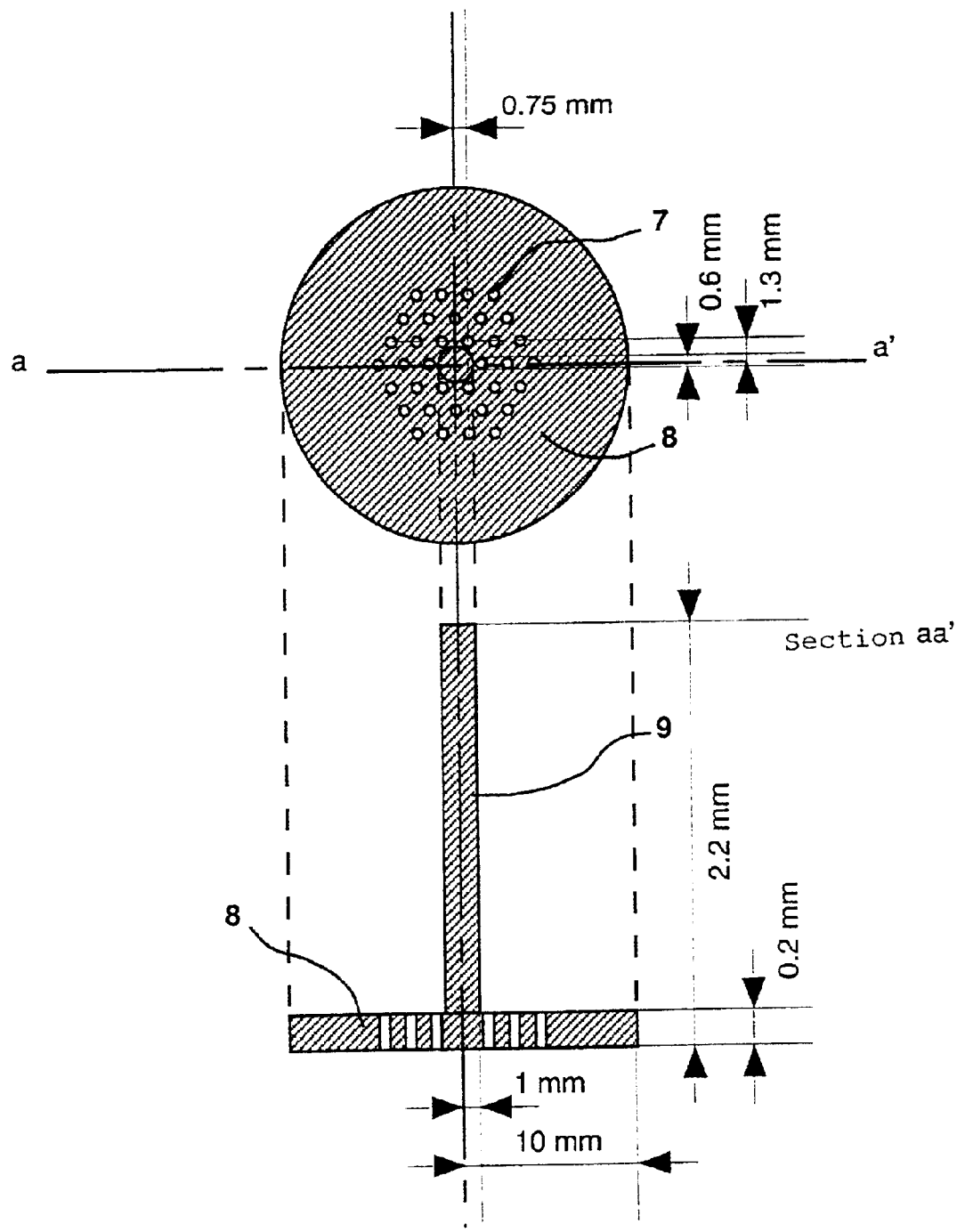

FIG. 4: Partial sketch of the setup used for producing the macroporous architecture of the bone substitute illustrated in previous figures.

Figure 5:
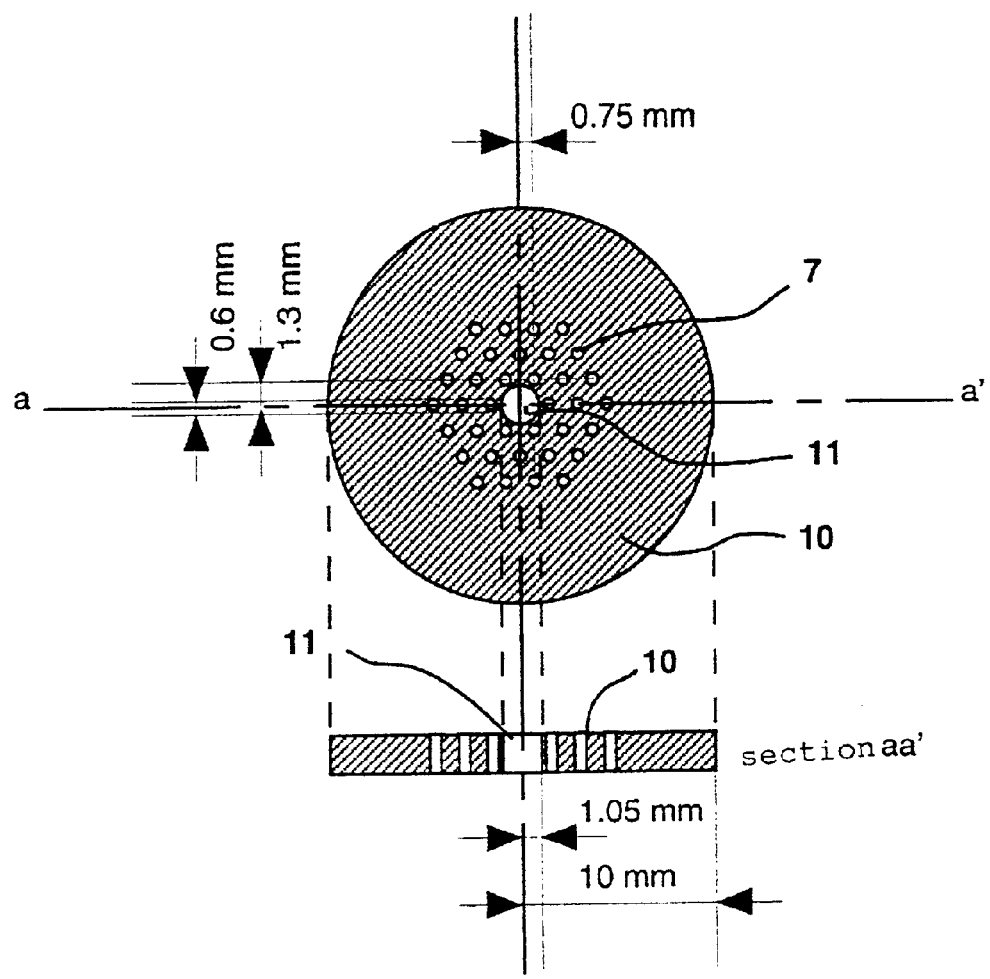

FIG. 5: Another partial sketch of the setup presented in FIG. 4.

Figure 6:
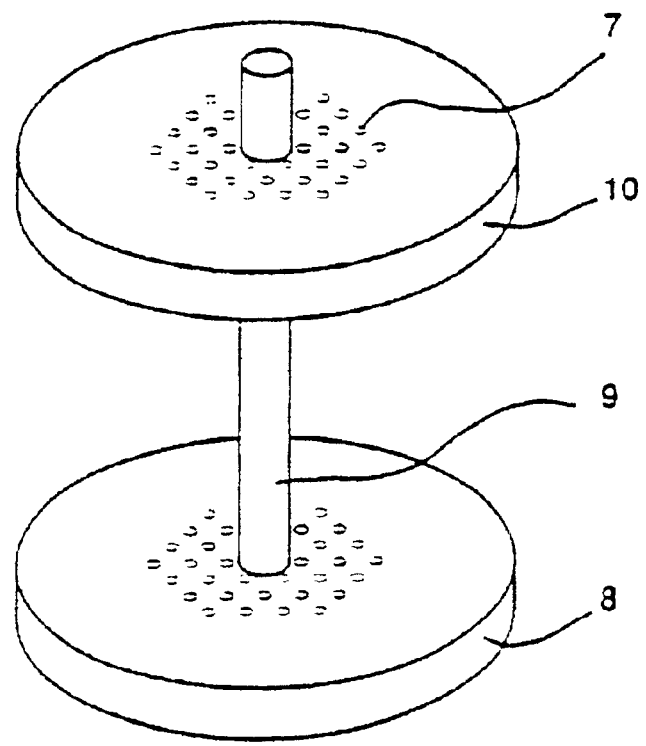

FIG. 6: Global sketch of the setup presented in FIG. 4.

Figure 7:
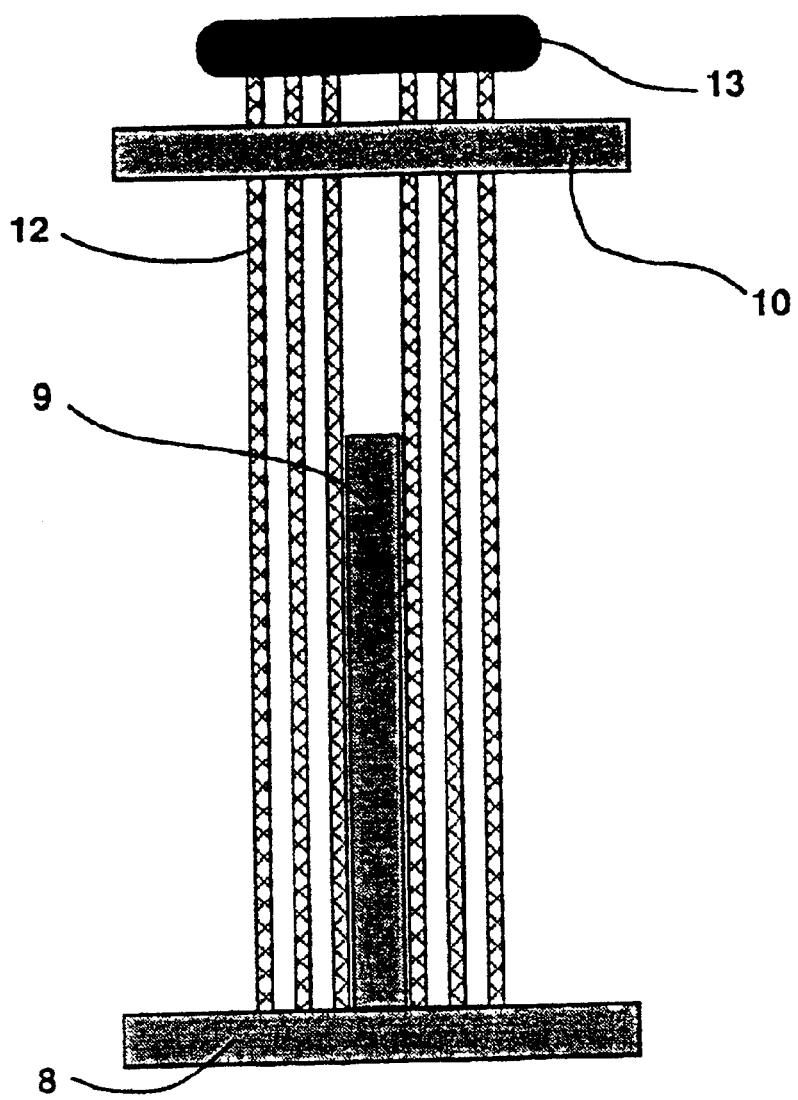

FIG. 7: Same setup as in FIG. 4, including polymer threads.

Figure 8:
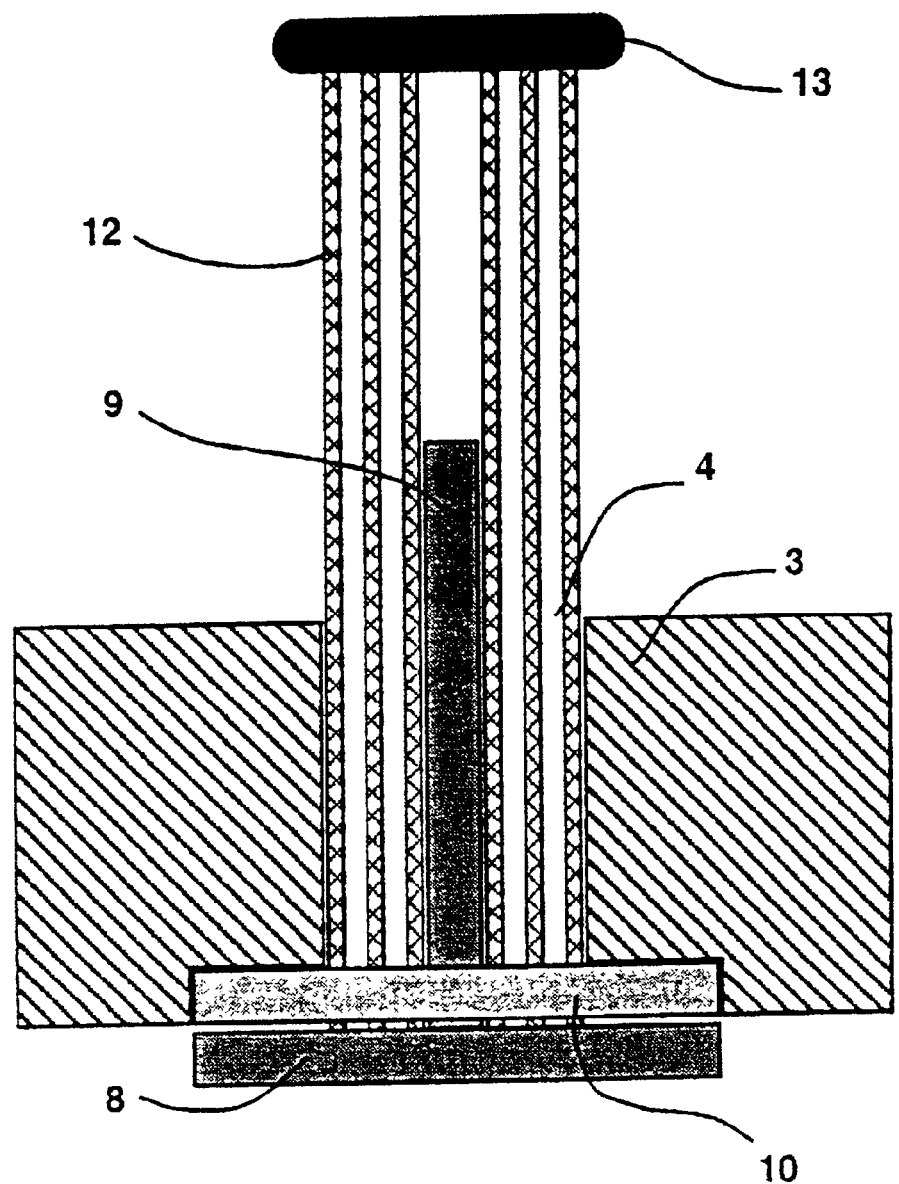

FIG. 8: Same setup as in FIG. 4, positioned in the mold of FIG. 3.

Figure 9:
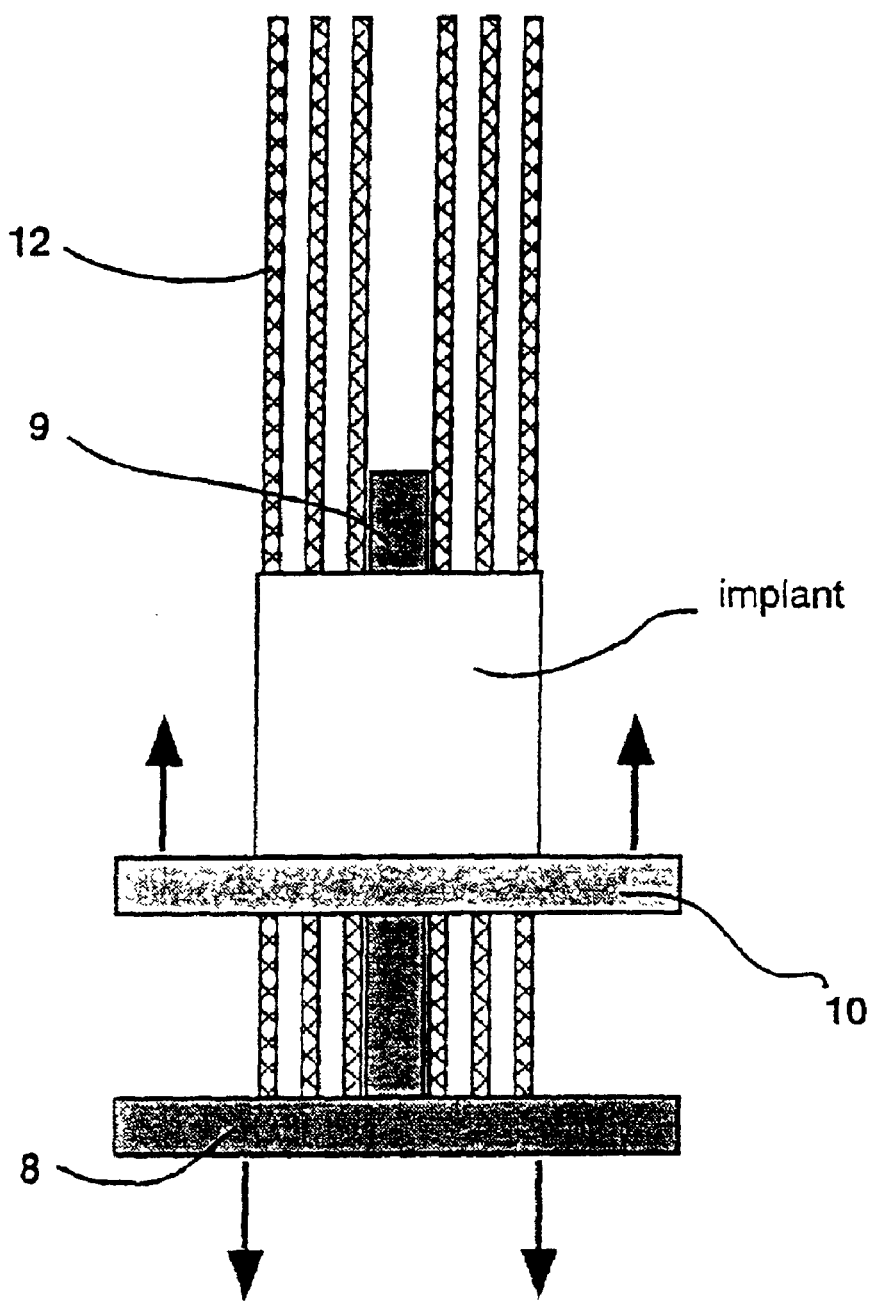

FIG. 9: Setup of FIG. 8 including after removal of the mold, showing removal of the porogenic threads from the bone substitute.

Figure 10:
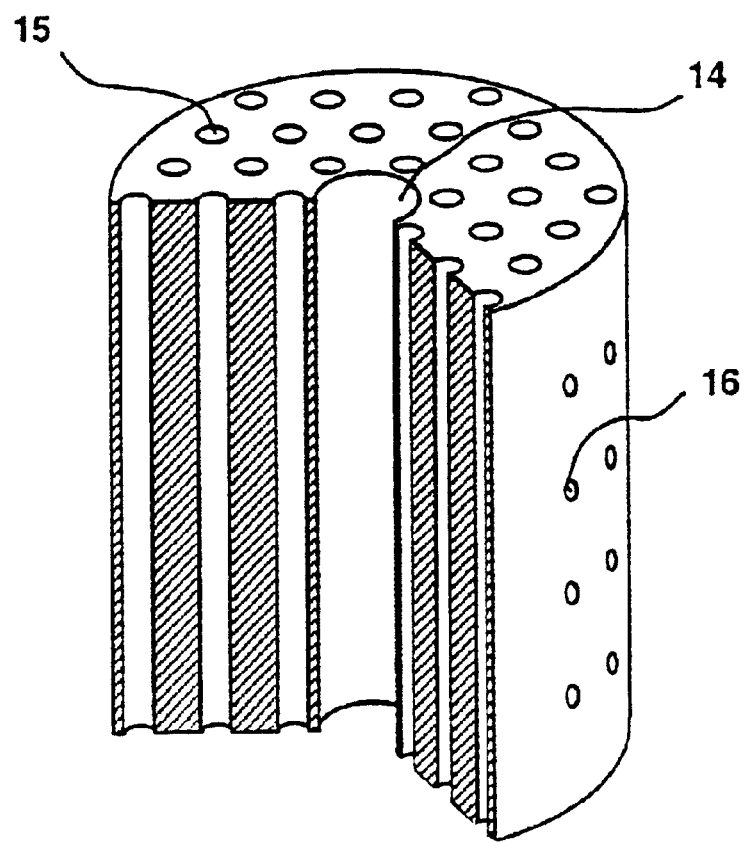

FIG. 10: Bone substitute according to a second variation of the present invention.

Figure 11:
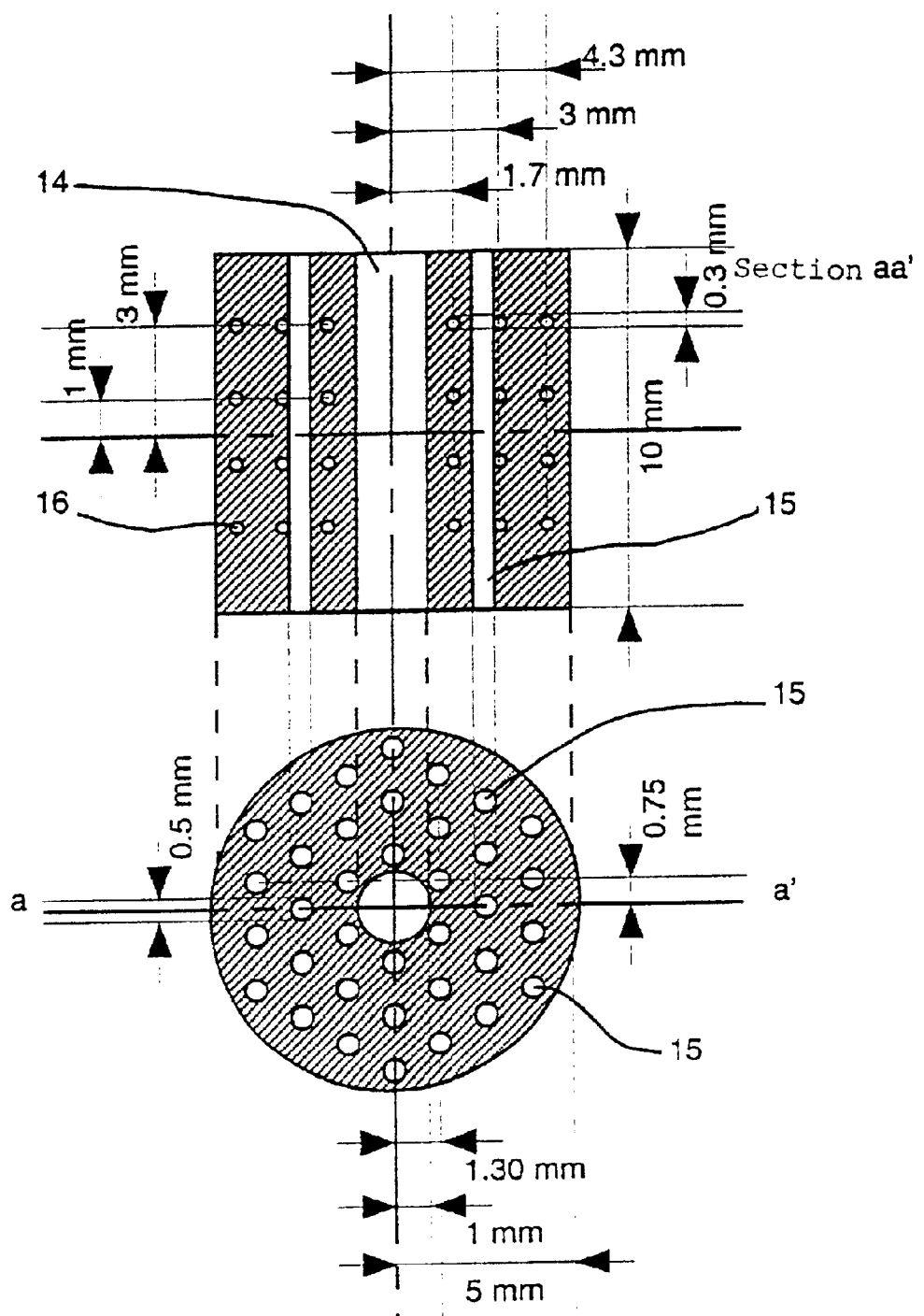

FIG. 11: Bone substitute of FIG. 10, upper and front views.

Figure 12:
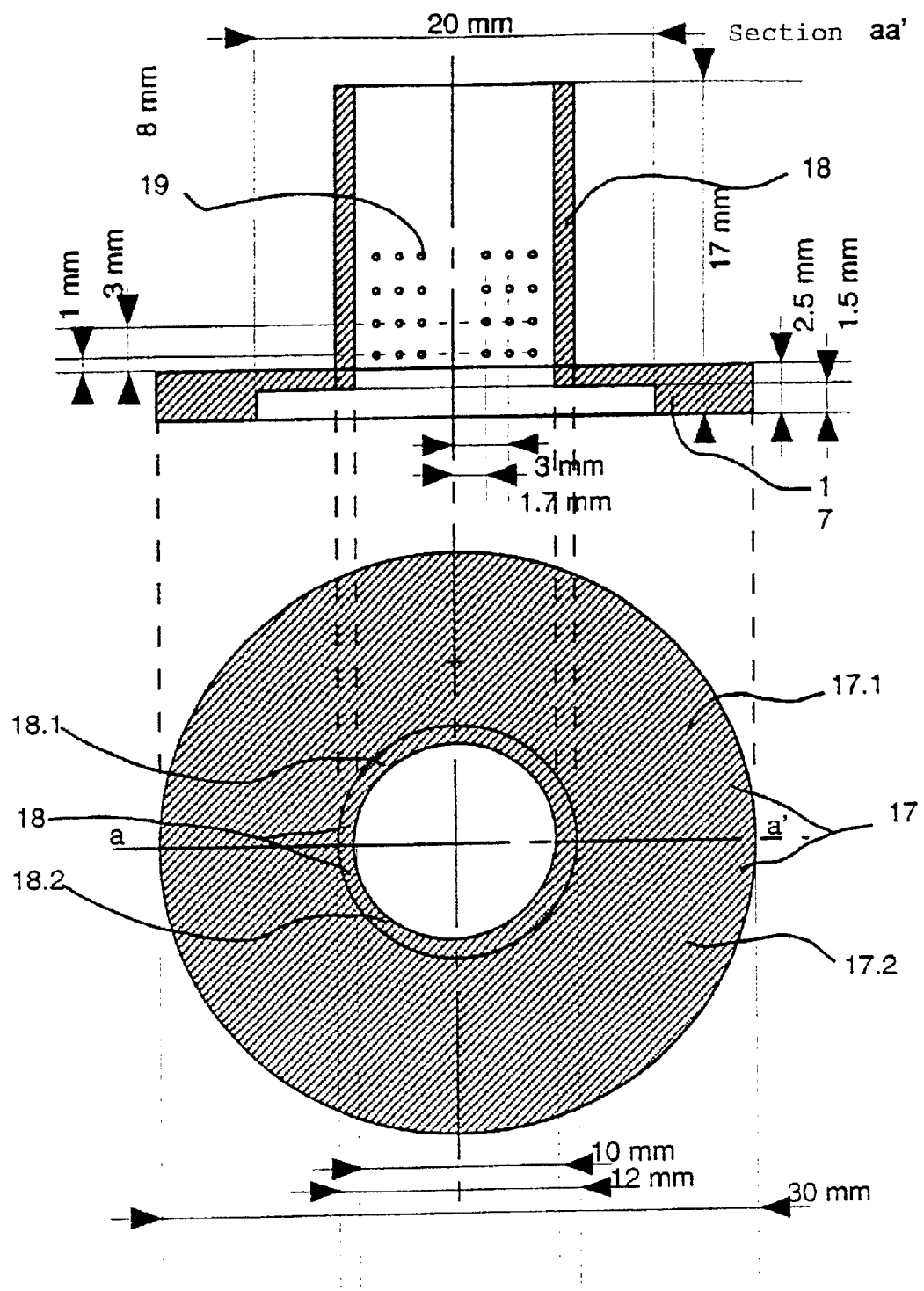

FIG. 12: Sketch of the mold used for producing the bone substitute illustrated in FIGS. 11.

Figure 13:
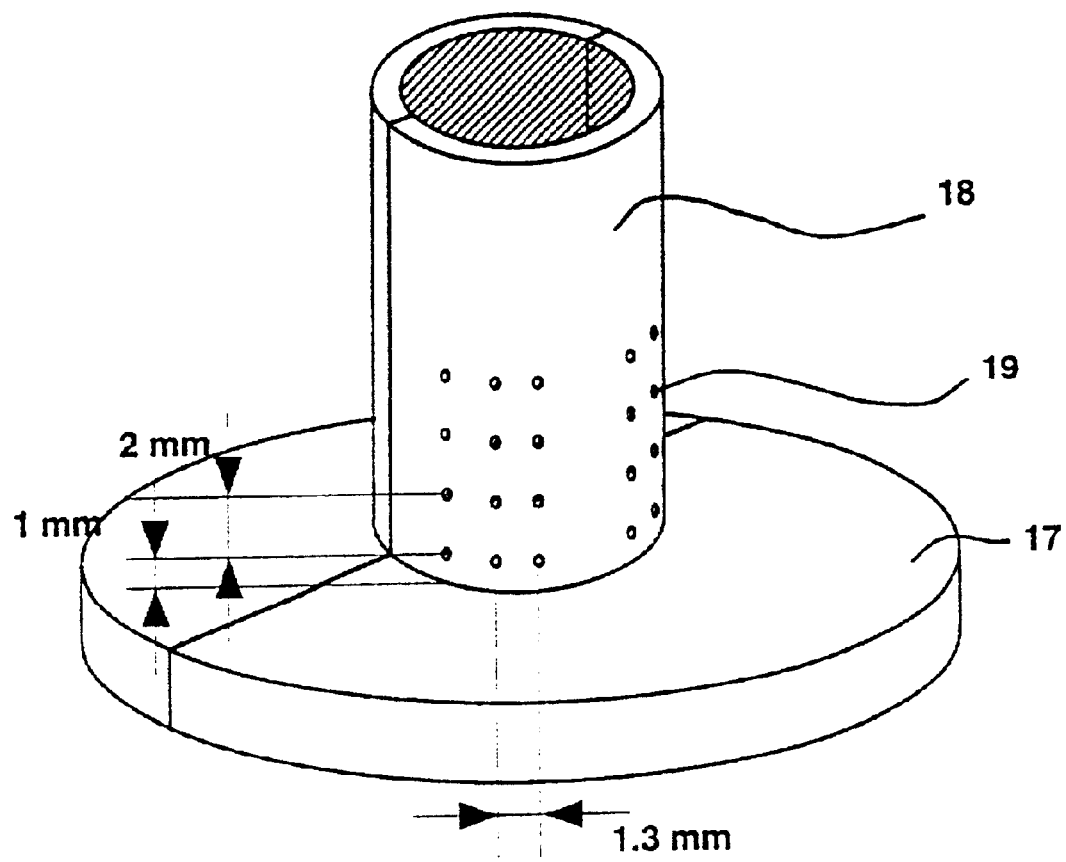

FIG. 13: Perspective view of the mold shown in FIG. 12.

Figure 14:
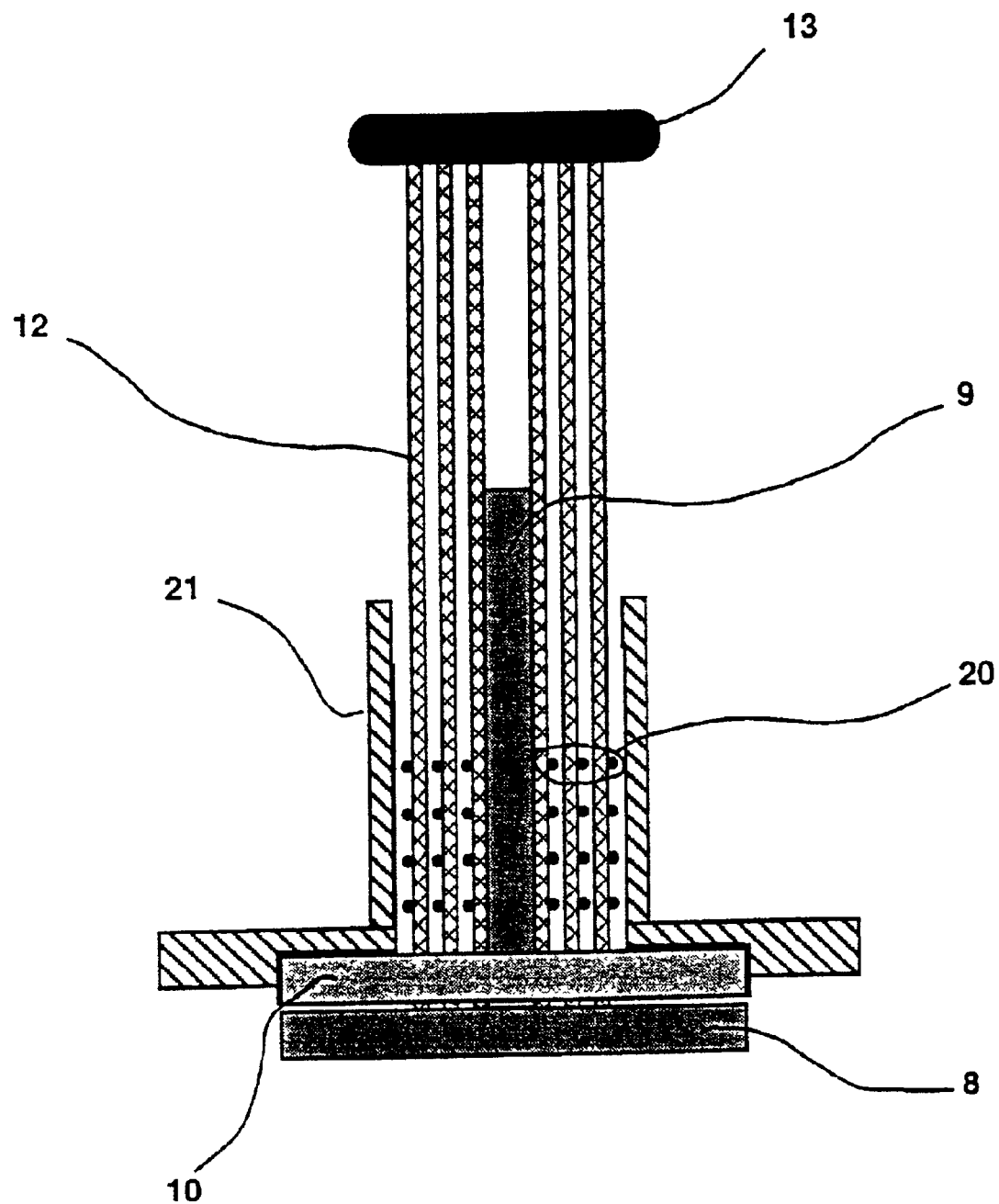

FIG. 14: Global view of the setup formed by the mold and the porogenic structure used for producing the bone substitute illustrated in FIGS. 10 and 11.

EXAMPLE 1

Cylindrical Bone Substitute Including a Unidirectional or Bidirectional Macroporous Architecture Made of Brushitic Cement.

The bone substitute is shaped by casting a liquid cement paste of the brushitic type into a mold made either of silicone rubber (unidirectional porosity) or of stainless steel (bidirectional macroporosity). The macroporous architecture is generated upon molding by polymer (e.g. nylon) or stainless steel threads (bidirectional macroporosity).

a) Bone substitute with unidirectional macroporosity.

Description of the Bone Substitute (FIGS. 1 and 2)

The bone substitute consists in a cylinder 10 mm in diameter and 10 mm height. A central channel (1) 2 mm in diameter is managed along the rotational axis of the substitute, simulating the medullar cavity of the bone to be replaced. The macroporous architecture consists in a main hexagonal network of cylindrical pores 0.5 mm in diameter (2), parallel to the axis of the bone substitute, the distance between the rotation axes of adjacent pores being 1.5 mm. This hexagonal macroporous network occupies approximately 9 to 10 volume % of the apparent volume of the substitute, after subtraction of the volume of the central channel. The brushitic cement formulation used develops a microporosity representing 31 volume % of the total solid volume (after subtraction of the macroporosity). Thus, the bone substitute of this example develops a total porosity comprised between 37 and 38 volume %.

Description of the Different Parts of the Molding Setup (FIGS. 3, 4 et 5)

The mold (3) consists in a single part of silicone rubber, produced by casting in a steel model. Two apertures with two different diameters (4, 5), and a lateral slit (6) are managed in the mold (FIG. 3). The setup used for producing the unidirectional macroporosity consists in two aluminum circular plates (FIGS. 4 and 5) perforated with 36 holes (7) 0.6 mm in diameter, which rotation centers are distant by 1.5 mm. These holes are designed for receiving polymer strands 0.5 mm in diameter and 40 mm long, which are used as porogenic phase. A rod (9) 2 mm in diameter is fixed in the lower plate, whereas the upper plate (10) presents a central bore (11) 2.1 mm in diameter (FIGS. 4 and 5).

Operating the Setup (FIGS. 6, 7 and 8)

The setup used for macroporosity generation is designed to be used several times. The upper plate (10) with the central hole can be moved along the rod (9) fixed to the lower plate (8) (FIG. 6). Polymer strands 40 mm long are individually thread through each of the 36 holes (7) of the two plates (8, 10). These strands are then glued to the lower plate (8), and the upper plate (10) is kept free to move along the rod fixed to the lower plate (8) and along the polymer strands (12). The polymer strands (12) are then tightened between the two plates in order to make a network of unidirectional parallel strands. The ends of the strands on the mobile plate side (10) are then dipped into a small container filled with fused wax. After solidification, the wax (13) keeps the strands in straight parallel positions (FIG. 7). The mobile plate (10) is then moved downwards along the rod (9) and the strands (12) until it comes in contact with the lower plate. The polymer strand network (12) is thus maintained in straight position by the two plates (8, 10) on one end, and by the solidified wax block (13) at the other end.

The polymer strand network is then inserted in the center hole of the solicone rubber mold (3) through its lateral slit (6). The setup is then carefully centered with respect to the mold axis, and the plate (10) is adjusted as foreseen into the lower aperture (5) of the silicone rubber mold (FIG. 8).

SYNTHESIS AND MOLDING OF THE BRUSHITiC CEMENT PASTE

The brushitic cement combines two calcium phosphate powders with water, and consolidates after mixing as a consequence of the following chemical reaction:

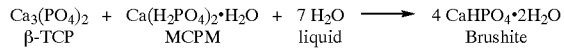

$Ca_3(PO_4)_2$ + $Ca(H_2PO_4)_2 \cdot H_2O$ + $7 H_2O$ ⟶ $4 CaHPO_4 \cdot 2H_2O$
β-TCP      MCPM      liquid      Brushite Without additives, this reaction is very fast and leads to complete consolidation within less than a minute at ambient temperature. Mixing the powders with a diluted aqueous solution of sulfuric acid ($H_2SO_4$, 0.1 mole/L) instead of water, and adding a precise amount of sodium pyrophosphate allows an accurate control of the setting time of the cement, which can then be adjusted within a 10–20 min range, in order to facilitate the molding process.

The solid/liquid ratio of the cement paste is fixed at 2.5 g/mL, in order to obtain a plastic paste well adapted to molding.

The cement mix is as follows:

- 1.2 g of β-tricalcium phosphate powder (β-TCP) with a calcium/phosphate atomic ratio comprised between 1.44 and 1.47; the powder has a median particle size of 2.5 μm and a specific surface area of approximately 2.5 m²/g
- 0.8 g of monocalcium phosphate monohydrate (MCPM).
- 0.015 g of dihydrogen disodium pyrophosphate ($Na_2H_2P_2O_7$).
- 1 mL of diluted aqueous $H_2SO_4$ (0.1M).

The mixing liquid, MCPM and $Na_2H_2P_2O_7$ are carefully kneaded in a mortar with a spatula. The β-TCP powder is then added to the mixture which is kneaded for approximately one minute, so as to obtain a thin homogeneous paste. At ambient temperature (19–20° C.), this paste should be used within 10 minutes after the addition of β-TCP.

After mixing, the cement paste is loaded in the barrel of a syringe, and injected into the rubber mold through its upper aperture (4). Cement injection is performed in successive steps, in order to ensure proper filling of the mold. Between two successive injections, the mold is vibrated during about 30 seconds, in order to eliminate air bubbles possibly entrapped in the cement paste. Successive injections are performed until complete filling of the mold.

Unmolding of the Bone Substitute (FIG. 9)

After full completion of the cement consolidation, the bone substitute is removed from the rubber mold trough the lateral slit (6). The wax block (13) is removed in order to liberate the ends of the polymer strands. The polymer strands are then removed by pulling the mobile plate (8) away from the fixed plate (10) (FIG. 9). The height of the bone substitute is adjusted to 10 mm by grinding.

b) Bone Substitute with Bidirectional Macroporous Architecture

Description of the Substitute (FIGS. 10 and 11)

The substitute consists in a hollow cylinder 10 mm in diameter and 10 mm in height. The central channel (12) 2 mm in diameter, coaxial to the substitute, mimicks the medullar cavity of the bone to be replaced. The macroporous architecture consists in two interconnected networks of elongated pores. The hexagonal main pore network (15) is identical to that of the unidirectional macroporous architecture presented previously. It consists in cylindrical pores at, 0.5 mm in diameter (2), parallel to the axis of the bone substitute, the distance between the rotation axes of adjacent pores being 1.5 mm. The cylindrical macropores of the secondary pore network (16) have a diameter of 0.3 mm. Their rotation axes are distant by 2 mm in the direction parallel to the axis of the substitute, and of 1.3 mm along a direction orthogonal to the same axis (section aa' of FIG. 1). The secondary pore network do not cross the central channel (14). The so obtained macroporous architecture occupies a total volume fraction of 10.2% of the substitute (excluding the central channel). Since the brushitic cement used in this example develops an intrinsic microporosity of 31 volume %, the total porosity of the substitute is approximately 38 volume %.

Description of the Parts of the Setup (FIGS. 4, 5, 12, 13 and 14)

The mold (FIG. 2) in stainless steel is made of four parts: two half-disks (17.1 and 17.2) which, after lateral apposition, form a circular base (17) 30 mm in diameter and 2.5 mm thick, with a central hole 10 mm in diameter; two hollow half-cylinders (18.1 and 18.2), each one being fixed on its respective half of the base. Each assembly (half-cylinder plus half-base) forms a half mold in stainless steel. After assembling the two half molds, a mold is formed consisting in a circular base (17) attached to a hollow cylinder (18) with the following dimensions: height 14.5 mm, inner diameter 10 mm, wall thickness 1 mm. 24 circular holes (19) 0.35 mm in diameter are drilled in the two half-cylinders (18.1 and 18.2) composing the hollow cylinder (18) (FIGS. 12 and 13). The rotation axes of these holes are regularly spaced at 2 mm intervals in the vertical direction and at 1.3 mm intervals in the horizontal direction. The setup used for making the main macroporous network is the same as for the bone substitute with unidirectional macroporosity (see FIGS. 4 and 5). It consists in two aluminum circular plates perforated with 36 holes (7) 0.6 mm in diameter, which rotation centers are distant by 1.5 mm. In these holes will be thread the polymer strands 0.5 mm in diameter and 40 mm long, used as porogenic phase. A rod (9) 2 mm in diameter is fixed in the lower plate (8) whereas the upper plate (10) includes a central hole (11) 2.1 mm in diameter.

Operating the Setup (FIGS. 6, 7 and 14)

The first operating step is identical to that used for the bone substitutes with unidirectional macroporous architecture (see FIGS. 6 and 7). The unidirectional strand network aimed at generating the main macroporous network is inserted between the two stainless steel half-molds, and carefully centered with respect to the rotation axis of the mold. Then, the plate (1) is adjusted into the lower aperture of the stainless steel mold.

A further step consists here in threading 24 stainless steel strands (20) 0.3 mm in diameter and 30 mm long through the 24 holes (19) bored tin the stainless steel mold (21) (FIG. 14). These strands form a second network of stainless steel strands orthogonal and interconnected to the main network of polymer strands (20), each steel strands coming in contact with a row of polymer strands of the main network.

Synthesis and Molding of a Brushitic Cement Paste Into the Mold

These two steps are the same as for the bone substitute with unidirectional macroporosity presented previously.

Unmolding the Bone Substitute

After consolidation is completed, the stainless steel strands (20) are pulled one after the other out form the substitute still contained in the mold. The two stainless steel half molds are then separated, releasing so the bone substitute. The wax block (13) is removed, releasing so the ends of the polymer strands. Finally, the polymer strands together with the central rod are carefully removed from the bone substitute by mere pulling of plate (8) while keeping plate (10) fixed. The height of the substitute is adjusted to 10 mm by grinding.

EXAMPLE 2

Bone Substitute in Calcium Phosphate Cement with Anatomic Shape and Macroporous Architecture Made by a Fast Prototyping Technique Based on Tridimensional Fused-Jet Printing (Apparatus Type Modelmaker II, Sanders Prototype, Inc.)

As the case may be, the wax construct made by fast prototyping is the positive or the negative of the anatomic shape of the desired bone substitute. The porogenic phase also produced by fast prototyping corresponds always to the negative of the macroporous architecture desired for the bone substitute. The design of the mold geometry and of the porogenic construct can be done on the basis of a digitized medical image possibly assisted by a Computer-Assisted Design (CAD) software. Complex macroporous architectures can be designed, for instance tridimensional networks of interconnected macropores. Moreover, the macroporous architecture can be designed so as to develop the best compromise between mechanical performance and fast bone colonization of the substitute. In the case of long bone defects, a central channel mimicking the medullar cavity of the bone defect can be designed in the bone substitute.

a) Bone substitute made of brushitic cement

A wax construct is made by tridimensional fused-jet printing. Its geometry corresponds to the negative of the anatomic shape and to the macroporous architecture of the bone substitute. Thus, the wax construct plays two roles; on one hand, it defines the outer shape of the substitute; on the other hand, it serves as porogenic phase, leaving the desired macroporous network in the bulk of the bone substitute after elimination of the wax. An upper aperture is planned during the design of the construct, through which the mold can be filled by injection of the brushitic cement. The procedures for preparing the cement paste and injecting it in the mold are identical as those described in Example 1. After completion of the cement consolidation, the wax is eliminated at low temperature by selective dissolution in a non aqueous solvent. Thus, a bone substitute with anatomic shape and well controlled macroporous architecture is obtained.

b) Bone substitute made of hydroxyapatite cement.

The bone substitute is shaped by casting a liquid paste of calcium phosphate cement into a plaster mold. Two half-molds are made by the lost-wax technique, using fast prototyping for making a wax model of the bone substitute: thus, tridimensional fused-jet printing is used for making two wax constructs, corresponding to two halves of the bone substitute. Those two wax constructs are separately immersed in liquid plaster. After complete plaster consolidation, the wax constructs are eliminated by selective dissolution in a non-aqueous solvent, leaving the two plaster half-molds. A third wax construct, corresponding to the negative of the desired macroporous architecture, is produced by tridimensional fused-jet printing. Its geometry is designed so as to match perfectly the walls of the plaster mold obtained by assembling the two half-molds discussed previously. The complete assembly composed of the two adjusted plaster half-molds and of the porogenic wax construct is used to make the bone substitute, by casting of a liquid calcium phosphate cement paste. The cement past consists in a stoechiometric mixture of powdery dicalcium phosphate anhydrous (DCPA) and calcium carbonate (calcite, CC) in an aqueous solution of 2% weight of sodium polyacrylate (0.5 mL of mixing solution per g of dry powder mixture). A green body is obtained by slow absorption by the plaster of the mold of the excess liquid of the cement paste. In order to compensate for drying shrinkage, feeding of the mold in liquid cement paste is maintained until complete consolidation of the bone substitute. After consolidation of the green bone substitute, the porogenic wax construct is eliminated by selective dissolution at low temperature in a non-aqueous solvent. The so obtained green body is then chemically consolidated in an autoclave. The chemical consolidation process occurs at 121° C. within 1 hour in a water-saturated atmosphere, according to the following reaction:

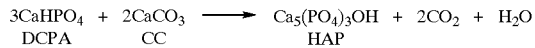

$$3CaHPO_4 + 2CaCO_3 \longrightarrow Ca_5(PO_4)_3OH + 2CO_2 + H_2O$$
$$\text{DCPA} \quad\quad \text{CC} \quad\quad\quad\quad \text{HAP}$$

The so obtained hydroxyapatite bone substitute shows perfectly controlled anatomic shape and macroporous architecture.

What is claimed is:

1. Bone substitute made in one piece from cementitious calcium phosphate materials chemically consolidated at low temperature in the presence of water, said bone substitute comprising a main network constituted of channels, characterized by the fact that it also includes at least a secondary channel network, said secondary channel network being interconnected to said main channel network, and wherein the channels are longitudinal and can be prepared with a predefined, controlled macroporosity.

2. Bone substitute according to claim 1, characterized by the fact that the total pore volume fraction is comprised between 28% and 88%.

3. Bone substitute according to claim 1, made of a material obtained by heating a mixture of dicalcium phosphate anhydrous (monetite, DCPA) and calcium carbonate (calcite, aragonite or vaterite) in a water-saturated atmosphere.

4. Process for manufacturing a bone substitute according claim 1, characterized by the fact that the cementitious mixture is consolidated through a chemical process taking place ex-vivo, either in ambient atmosphere at ambient temperature, or at higher temperatures in a water-saturated atmosphere.

5. Process for manufacturing a bone substitute according to claim 1, characterized by the fact that the anatomic shape and the internal macroporous architecture of said bone substitute are obtained during the molding process of a calcium phosphate cementitious paste and the chemical consolidation ex-vivo of said cementitious paste.

6. Process for manufacturing a bone substitute according to claim 1, characterized by the fact that the channels are made using threads made of polymers such as nylon, PVB or polyethylene.

7. Process for manufacturing a bone substitute according to claim 1, characterized by the use of a rapid prototyping technique, comprising stereolithography or fused-jet tridimensional printing, for making the mold and the porogenic architecture of said bone substitute.

8. Bone substitute according to claim 1, characterized by the fact that the main channel network is made of parallel channels.

9. Bone substitute according to claim 8, characterized by the fact that the channel sections of the secondary channel network is comprised between $3.10^{-3}$ et $8.10^{-3}$ $mm_2$.

10. Bone substitute according to claim 1, characterized by the fact that the volume fraction of the channels is comprised between 10% and 70%.

11. Bone substitute according to claim 10, characterized by the fact that the volume fraction of the channels is comprised between 30% and 60%.

12. Bone substitute according to claim 1, made from a liquid or plastic paste comprising at least one calcium phosphate and at least one further sparingly soluble calcium salt such as sulfate, pyrophosphate or carbonate.

13. Bone substitute according to claim 12, obtained from a mixture comprising: (a) β-tricalcium phosphate (β-TCP) and monocalcium phosphate monohydrate (MCPM); (b) tetracalcium phosphate monoxide (higenstockite, TTCP) and dicalcium phosphate dihydrate (brushite, DCPD) or dicalcium phosphate anhydrous (monetite, DCPA); (c) α-tricalcium phosphate (α-TCP) and monocalcium phosphate monohydrate (MCPM); or (d) dicalcium phosphate anhydrous (monetite, DCPA) and calcium carbonate (calcite, aragonite or vaterite).

14. Bone substitute according to claim 1, characterized by the fact that the channel(s) of the main channel network is/are oriented along the directions of the main mechanical stresses that said bone substitute will have to bear after implantation in a physiological environment.

15. Bone substitute according to claim 14, characterized by the fact that the channel section of the main channel network is comprised between $8.10^{-3}$ et 0.8 $mm^2$.

16. Bone substitute according to claim 4, characterized by the fact that the channel section of the main channel network is comprised between 0.1 et 0.3 $mm^2$.

* * * * *